United States Patent [19]

Leong et al.

[11] Patent Number: 5,156,843
[45] Date of Patent: Oct. 20, 1992

[54] FABRIC IMPREGNATED WITH FUNCTIONAL SUBSTANCES FOR CONTROLLED RELEASE

[75] Inventors: Helen C. Leong, Atherton; Martin Katz, Menlo Park; Chung-Heng Cheng, San Jose, all of Calif.

[73] Assignee: Advanced Polymer Systems, Inc., Redwood City, Calif.

[21] Appl. No.: 326,139

[22] Filed: Mar. 20, 1989

[51] Int. Cl.$^5$ ............... A01N 25/08; A01N 25/34; A61L 9/04; B32B 5/16
[52] U.S. Cl. ................... 424/411; 424/400; 424/401; 424/402; 424/403; 424/404; 424/405; 424/409; 424/414; 424/416; 424/501; 424/502; 424/59; 424/76.3; 514/963; 514/965; 428/241; 428/243; 428/281; 428/905; 428/907; 428/911; 428/913
[58] Field of Search ............ 424/402, 414, 416, 501, 424/502, 411, 400, 401, 403, 404, 405, 409, 59, 76.3; 514/963, 965; 428/241, 243, 281, 905, 907, 911, 913

[56] References Cited

U.S. PATENT DOCUMENTS

| | | | |
|---|---|---|---|
| 3,896,807 | 7/1975 | Buchalter | 424/402 |
| 4,427,793 | 1/1984 | Reed et al. | 521/31 |
| 4,514,461 | 4/1985 | Woo | 428/240 |
| 4,690,825 | 9/1987 | Won | 424/501 |
| 4,706,470 | 11/1987 | Bouchette | 424/402 |
| 4,904,524 | 2/1990 | Yoh | 424/402 |

FOREIGN PATENT DOCUMENTS

| | | |
|---|---|---|
| 0041934 | 12/1981 | European Pat. Off. . |
| WO79/00014 | 1/1979 | PCT Int'l Appl. . |
| 2080814 | 2/1982 | United Kingdom . |

OTHER PUBLICATIONS

"Impregnating Fabrics with Microcapsules", Schaab, pp. 84–85.
C. K. Schaab, "Impregnating Fabrics With Microcapsules", *HAPPI*, May 1986.
C. K. Schaab, "Impregnating Nonwoven Fabrics With Microencapsulated Components", *Nonwovens Industry*, Nov. 1985.

*Primary Examiner*—Thurman K. Page
*Assistant Examiner*—Carlos Azpuru
*Attorney, Agent, or Firm*—Townsend and Townsend

[57] ABSTRACT

Intersticed materials, including woven and nonwoven fabrics, open-cellular materials and the like, are impregnated with functional substances by incorporating the substances in microscopic porous particles in which the pores form an interconnected network open to the particles in the interstices of the materials. The functional substances thus impart useful properties to the material in a controlled release manner.

32 Claims, No Drawings

FABRIC IMPREGNATED WITH FUNCTIONAL SUBSTANCES FOR CONTROLLED RELEASE

This invention relates to woven and nonwoven fabrics, and in general all such materials provided with interstices, such as pads, filters, porous liner materials, garment inserts, prosthetics and prosthetic supports, bandages, and cloth of various types. The invention further relates to controlled release technology, and the application of this technology to these types of materials.

BACKGROUND OF THE INVENTION

Information relevant to the present disclosure may be found in Won, U S. Pat. No. 4.690.825 (issued Sep. 1, 1987). Woo. U.S. Pat. No. 4,514,461 (Apr. 30, 1985). and pending U S. patent applications Ser. No. 07/091,641 (filed Aug. 31, 1987) abandoned and Ser. No. 07/197,375 (filed May 23, 1988) now U.S. Pat. No. 4,873,091 both commonly assaigned herewith.

The use of fabrics, sponges, and other porous, absorbent or intersticed materials as a means for retaining functional substances is known The functional substances may range widely in character. and serve a wide range of purposes, including therapeutic, cosmetic. hygienic, and preventive functions. Examples of products embodying such materials are personal care products, cosmetics, toiletries, fragrances, pharmaceutical products, and household and industrial products, in either permanent, semi-permanent or disposable form.

An important feature of many such products is their ability to extend their utility over a long period of time by retaining sizeable quantities of the functional ingredients while exposing only a portion of them to the surroundings where they are available for use. Control of the release rate is achieved in a variety of ways. including diffusion through the interstitial network, forcing the ingredient to the surface by compression of the interstices, and rupture of internal bubbles or cells in the matrix material.

These mechanisms rely considerably on the structure of the matrix material itself, and this places limitations on the selection of the material as well as its properties.

SUMMARY OF THE INVENTION

The present invention provides a novel method of impregnating fabrics and other intersticed materials with functional substances in a controlled-release manner. where the primary controlling element is independent of the fabric matrix. In accordance with this invention. the functional substance is retained in the pores of microscopic porous particles, the particles being of an inert solid material and the pores being interconnected and open to the particle surface. The particles thus retain the functional ingredient within their pores and yet provide continuous pathways for travel of the substance to the particle surface for release into the fabric matrix and ultimate release to the surroundings.

Travel of the functional ingredients through the pores and out of the particles may be driven by diffusion, volatilization, pressure, or agitation. Release may be gradual when simple diffusion or volatilization is involved. or upon demand when pressure or agitation are involved, or a combination. The particles themselves are either rigid (i.e., substantially noncompressible) or compressible. The entrapped substance may be fluid, including both volatile and nonvolatile liquids or solutions, a solvent-soluble or low-melting solid, or a semi-solid. Release upon demand may be achieved, depending upon the product characteristics, by pressure, by rubbing the article over a surface to which the functional substance is to be applied, by the use of externally applied heat such as for example for articles designed to be placed in proximity to portions of the human body. or by contact with solvents, bodily secretions or other liquids in general. The use of the particles as retaining means for these substances provides a higher degree of control over their release than in systems where the fabric matrix is impregnated directly with the substances. When release is diffusion-controlled, it occurs in a more sustained manner, providing a continuous fresh supply to the fabric matrix and thus to the atmosphere in which the matrix is placed or the surface with which the matrix is placed in contact. Since the parameters controlling the release rate in diffusion-controlled applications are the pore volume distribution in the particle. notably its total pore volume and average pore diameter. these parameters may be selected as a means of adjusting the release rate to particular levels. A further advantage is the ability of the system to spread a small amount of the functional substance over a large matrix volume in a substantially uniform manner, thereby avoiding waste and further controlling the release rate and capacity of the matrix. Still further. by reducing the exposure of the functional substance to the atmosphere, the system of the invention is particularly useful for irritating or toxic volatiles. by reducing the rate of volatilization. A still further advantage is seen in products where the liquids are detrimental to the structure of the tissue. wipe or fabric, causing it to shred, tear or otherwise fall apart. The present invention avoids this problem by incorporating the liquid into the particles.

Further objects and advantages of the invention will become apparent from the description which follows.

DETAILED DESCRIPTION OF THE INVENTION AND PREFERRED EMBODIMENTS

The particles used in connection with the present invention may either be rigid or resiliently compressible in character. In either case, they are penetrated with interconnected pores open to the particle surface, providing substantially full communication between the internal pore space and the particle exterior. The particles will be selected of a material which is inert with respect to the substances which come in contact with it, i.e.. both the fabric matrix and the functional material residing in the particle pores. The particle material may thus be chemically or biologically inert or both.

The particles are frequently spherical in shape, due to the use of suspensipn polymerization as a preferred method of preparation. The resulting microspheres may vary widely in size. Those falling within the range of about one to about 100 microns in diameter, particularly from about 10 to about 40 microns, are preferred.

The pore dimensions within the particles may also vary widely. with optimum dimensions depending on the chemical characteristics of the polymers used to form the particles as well as the diffusive characteristics of the functional substance retained inside. Different systems will thus call for different optimum ranges of pore volume distribution to obtain the most desirable properties for the ultimate product. In general, however, best results are obtained with total pore volumes ranging from about 0.01 to about 4.0 cc/g. preferably from about 0.1 to about 2.0; surface areas ranging from about 0.1 to about 500 m$^2$/g preferably from about 1 to about 400: and average pore diameters ranging from about 0.001 to about 1.0 micron, preferably from about 0.003 to about 3.0 micron. Following conventional methods of measuring and expressing pore sizes. the pore diameters are measured by techniques such as nitrogen adsorption isotherms or mercury intrusion and are based on the model of a pore of cylindrical shape.

The particles are conveniently formed by suspension polymerization in a liquid-liquid system. In general, a solution containing monomers and the functional or active ingredient is formed which is immiscible with water. An inert liquid. which may be the functional active ingredient and/or co-solvent or coupling agents, and which is fully miscible with the solution but immiscible with water is included in the solution. This phase or solution is then suspended with agitation in an aqueous phase which generally contains additives such as surfactants and dispersants to promote the suspension. Once the suspension is established with discrete droplets of the desired size. polymerization is effected, typically by activating the monomers by either catalysis or increased temperature or irradiation. Once polymerization is complete, the resulting solid particles are recovered from the suspension. If the inert liquid has been included. the particles are solid porous structures; the polymer having formed around the inert liquid, thereby forming the pore network. The liquid has accordingly served as a porogen, or pore-forming agent. and occupies the pores of the formed particles.

In certain cases, the functional substance itself may serve as the porogen, in which case the porous beads recovered from the suspension immediately after polymerization are substantially ready for use, following removal of surface moisture, and any further processing steps of this nature. In these cases. particle formation and incorporation of the functional substance are performed in a single step. This may accordingly be termed a one-step procedure. Functional substances which can be used in this manner are those which meet the following criteria.

1. They are either fully miscible with the monomer mixture or capable of being made fully miscible by the addition of a minor amount of non-water-miscible solvent;
2. They are immiscible with water, or at most only slightly soluble: and
3. They are inert with respect to the monomers, and stable when in contact with any polymerization catalyst used and when subjected to any conditions needed to induce polymerization (such as temperature and radiation).

For functional substances which do not meet these criteria, their placement inside the pores may be achieved by impregnation of preformed dry porous polymer particles. The product is thus prepared in two steps performed in sequence, the polymerization being performed first with a substitute porogen which is then removed and replaced by the functional substance. Materials suitable as substitute porogens will be liquid substances which meet the above criteria and which have the further characteristic of being readily extracted from the pore network of the particles once polymerization is complete. This covers a wide range of substances. notably inert. nonpolar organic solvents. Some of the most convenient examples are alkanes cycloalkanes. and aromatics. Examples of such solvents are alkanes of 5 to 12 carbon atoms, straight or branched chain. cycloalkanes of 5 to 8 carbon atoms. benzene, and alkyl-substituted benzenes such as toluene and the xylenes. Porogens of other 30 types include $C_5-C_{15}$ alcohols benzoate, perfluoro polyethers, and silicone oils. Examples of silicone oils are polydimethylcyclosiloxane, hexamethyldisiloxane, cyclomethicone, dimethicone, amodimethicone, trimethylsilylamodimethicone, polysiloxane-polyalkyl copolymers (such as stearyl dimethicone and cetyl dimethicone), dialkoxydimethylpolysiloxanes (such as stearoxy dimethicone), polyquaternium 21, dimethicone propyl PG-Betaine. dimethicone copolyol and cetyl dimethicone copolyol.

Once polymerization is complete, the porogen may be removed by solvent extraction, evaporation, or similar conventional operations.

A further advantage of the use of this twostep process is that it permits the removal of unwanted species from the polymerized structures prior to impregnation with the functional substance. Examples of unwanted species include unreacted monomers, residual catalyst, and surface active agents and/or dispersants remaining on the sphere surfaces. A further advantage of this technique is that it permits one to select the amount and type of porogen as a means of controlling the pore characteristics of the finished bead. One is thus no longer bound by the limitations of the functional substance as they affect the structure of the particle itself. This also permits partial rather than full filling of the pores with functional substance. and further control over pore size and distribution by selection among swelling and nonswelling porogens.

Extraction of the porogen and its replacement with (i.e.. impregnation of the dry particle with) the functional substance in the two-step procedure may be effected in a variety of ways. depending on the chemical nature of the porogen and its behavior in combination with that of the other species present. The particles are first recovered from the suspension by filtration, preferably using vacuum filtration apparatus (such as a Buechner funnel). The particles are then washed with an appropriate solvent to remove organic species not bound to the polymer, including surfactants having deposited on the particle surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used— i.e., where the porogen, unreacted monomer and water will form an azeotrope. In these cases, steam distillation is an effective way of extracting porogen from the beads. This again may be followed by drying under vacuum.

Once the particles are rendered dry and free of the substitute porogen and any unwanted organic materials, they are impregnated with the functional substance according to conventional techniques. The most convenient such technique is contact absorption. aided by solvents if necessary to enhance the absorption rate.

Functional substances which are solid at ambient conditions may be first melted by heating, then held in the molten state during the contact absorption. Once impregnation has occurred. the particles may be cooled to ambient temperature and the molten substances thus returned to solid form.

Certain functional substances may also be combined in a eutectic mixture to produce a low-melting composition usable in a manner similar to that of a melt. Melts and eutectics in general may be used in either the one-step or two-step procedure.

The polymerization process and the various parameters and process conditions involved can be selected and adjusted as a means of controlling the pore characteristics and consequently the capacity and release characteristics of the ultimate product. For example, proper selection of the cross-linking means, the amount and type of cross-linking agent. and the amount and type of porogen are means of attaining such control. Certain polymerization conditions may also be varied to such effect, including temperature, degree of radiation where used, degree of agitation and any other factors affecting the rate of the polymerization reaction.

Cross-linking in the polymer formation is a major means of pore size control. Monomers which may be polymerized to produce cross-linked polymer particles in accordance with the present invention include polyethylenically unsaturated monomers. i.e.. those having at least two sites of unsaturation, and monoethylenically unsaturated monomers in combination with one or more polyethylenically unsaturated monomers. In the latter case, the percentage of cross-linking may be controlled by balancing the relative amounts of monoethylenically unsaturated monomer and polyethylenically unsaturated monomer.

Monoethylenically unsaturated monomers suitable for preparing rigid or noncompressible particles include ethylene, propylene, isobutylene, diisobutylene, styrene, ethylvinylbenzene, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters: vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isopropene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithio-derivatives of glycols, and of resorcinol; divinylketone. divinylsulfide, allyl acrylate, diallyl maleate, diallyl fumarate, diallyl succinate, diallyl carbonate, diallyl malonate, diallyl oxalate diallyl adipate, diallyl sebacate, divinyl sebacate. diallyl tartrate diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

Particularly preferred rigid particles for the present invention are formed by the copolymerization of styrene and divinylbenzene, vinyl stearate and divinylbenzene, or methylmethacrylate and ethylene glycol dimethylmethacrylate. Usually the monoethylenically unsaturated monomer will be present at from about 20% to 80% of the monomer mixture, with the polyethylenically unsaturated monomer forming the remainder of the mixture. Particularly preferred is a styrene-divinylbenzene polymer which consists essentially of a hydrocarbon backbone with benzene rings and which is substantially completely free from reactive groups.

Resilient compressible particles for use in the present invention may be formed by the use of curable elastomers. Preferred such elastomers are those which are curable by cross-linking. Examples include isoprene rubbers. butadiene rubbers, chloroprene rubbers, isobutylene-isoprene rubbers, nitrile-butadiene rubbers, styrene-butadiene rubbers, and ethylene-propylene-diene terpolymers. Among these groups, the preferred are ethylene-propylene-diene terpolymers. The diene monomers in these rubbers cover a wide range of structures, including straight-chain diolefins, cyclic dienes and bicyclic dienes including bridged ring dienes. Examples of such dienes are 1,4-hexadiene and longer chain analogs and homologs thereof, dicyclopentadiene, and ethylidene norbornene (notably 5-ethylidene-2-norbornene). Each of the latter two contain a bridged ring, and their structures are as follows:

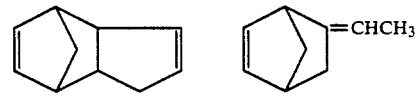

In further preferred embodiments of the invention, the rubber is an ethylene-propylene-diene rubber which has been prepared from an ethylene-propylene-diene (EPDM) prepolymer, cured according to conventional techniques. Preferred such prepolymers are those having a molecular weight ranging from about 1000 to about 30,000, preferably from about 5000 to about 10,000: and an iodine number (representing the degree of unsaturation in the molecule) ranging from about 5 to about 50, preferably from about 8 to about 30.

For EPDM rubbers, preferred polymerization catalysts or curing systems are free radical initiators, notably peroxide-type free radical initiators. Examples of peroxide initiators are tert-butyl perbenzoate, tert-butyl hydroperoxide, tert-butyl peracetate, 2,5-di(benzoylperoxy)-2,5-dimethylhexane, di-tert-butyl diperoxyazelate, tert-butyl peroxy-2-ethylhexanoate, tert-amyl peroctoate, 2,5-di(2-ethylhexanoylperoxy)- -2,5-dimethylhexane, and tert-butyl peroxyneodecanoate. Peroxyester initiators are preferred. In many cases, it will be advantageous to include polyfunctional active olefins in the reaction mixture as additives to improve peroxide cross-linking efficiency. Examples are dimethylolpropane trimethacrylate, trimethylolpropane trimethacrylate, ethylene glycol dimethacrylate, triallyl cyanurate, zinc acrylate, N,N'-meta-phenylenedimaleimide and polybutadiene. Preferred such olefins are dimethylolpropane trimethacrylate and trimethylolpropane trimethacrylate. In addition, metal soaps may be included as processing aids. Examples are naphthenates of sodium, potassium, manganese, lead, aluminum, magnesium, zinc, calcium, barium, cobalt, nickel, copper, iron and cesium; as well as octanoates of magnesium, zinc, manganese, calcium, barium, bismuth, lead, cobalt, iron and zirconium. Preferred metal soaps are cobalt naphthenate, manganese naphthenate and bismuth octoate.

For both rigid and compressible particles, the functional substances to be placed inside the pores may be dissolved in solvents to facilitate absorption into the pores. These solvents must be inert with respect to the particles themselves, and the particles must be insoluble in these solvents. The solvents most appropriate for any given system will depend on the materials from which the particles in that system are made as well as the functional substance to be placed inside the pores. With these considerations in mind, the selection is well within the ability of the skilled technician. Examples of organic solvents which will be appropriate depending on the systems used are liquid petrolatum, petroleum ether, ethanol (especially for menthol and thymol) higher alcohols (especially for camphor), isopropyl myristate, and diisopropyl adipate.

Once absorption has oocurred, the solvent can be evaporated or, if desired, retained together with the functional substance inside the pores. Other formulating materials, such as carriers or adjuvants and the like can also be present, and will be incorporated into and onto the particles together with the substances of interest and any other materials present.

The functional substances themselves may be either pure species, mixtures, solutions, suspensions or dispersions. Preferred forms are liquids, including volatile liquids, and low-melting solids. The substances may be biologically active substances for clinical or therapeutic utility, such as corticosteroids, vitamins, anesthetics and therapeutic drugs in general; prophylactic or biocidal substances, such as to prevent conception, to prevent the transmission of disease or infection, or to prevent or retard bacterial, microbial, germ or fungal growth; substances of a personal care nature, such as deodorants, moisturizers, emollients, lubricants, sunscreens, anti-acne agents, astringents or antiseptics; substances serving an aesthetic function, such as to impart flavors or fragrances; and substances of a household or industrial nature, such as cleaning solvents, detergents, waxes, polishes, insect repellents, flea and tick repellents and pesticides in general, mildew retardants or flame retardants.

The functional substance should comprise between approximately 5% and approximately 65% of the total weight of the impregnated particles.

Intersticed materials inside which the particles may be placed include for example curtains and drapes, upholstery, rugs and carpeting, clothing, insoles, linens, towels, diapers, sanitary napkins, tampons, cotton swabs, sponges, absorbent pads, polishing cloths and wiping cloths. In general, such materials include naturally-occurring materials and synthetics, fibrous materials and open-cellular materials, and woven and nonwoven fabrics.

The amount of impregnated particles held within the interstices of such materials may vary widely, depending on the utility and purpose of the impregnant as well as the nature of the matrix material. Optimum levels may exist in certain applications, and this will be readily apparent to those skilled in the art. In most cases, the impregnated particles will comprise from about 0.5% to about 60% by weight of the total product, preferably, from about 0.5% to about 50%.

The following example is offered strictly for illustrative purposes, and is intended neither to limit nor define the invention in any manner.

EXAMPLE

This example demonstrates the release characteristics of the functional substance nonoxynol 9 from two types of microscopic porous particles, one formed by the copolymerization of methyl methacrylate and ethylene glycol dimethacrylate (MMA/EGDMA) and the other formed by the copolymerization of styrene and divinylbenzene (S/DVB). Nonoxynol 9 is a poly(ethylene glycol) p-nonylphenyl ether with nine ethylene glycol units. used in spermicidal compositions.

To prepare the particles. a solution of nonoxynol 9 in isopropanol at a concentration of 35% by weight was combined with porous polymeric microbeads of the above two types. the beads themselves having been formed in accordance with techniques described in copending, commonly assigned U.S. Patent application Ser. No. 07/091,641, filed Aug. 31, 1987. The characteristics of the microbeads were as follows:

|  | MMA/EGDMA | S/DVB |
| --- | --- | --- |
| Microbead Diameter (microns, average) | 20 | 20 |
| Pore volume (cc/g) | 0.71 | 0.95 |
| Surface area (m$^2$/g) | 154 | 126 |
| Pore diameter (micron, average) | .02 | .03 |
| Nonoxynol 9 content (weight percent) | 40 | 40 |

The release rate of the nonoxynol 9 was determined using a 1000-mL vessel immersed in a water bath which maintained the temperature at 22 ±5° C. The apparatus further included a detachable basket fabricated of welded-seam, 5-micron mesh stainless steel cloth, formed into a cylinder 3.66 cm in height and 2.5 cm in diameter, attached to a metallic shaft connected to a variable speed drive.

Distilled water (500 mL) was placed in the vessel, and the impregnated beads (0.1000 mg) were placed in the basket. The basket was lowered into the water and stirring was begun at 500 rpm. Samples of 5 mL each were taken at 0.25., 0.5., 0.75., 1.0, 1.5, 2.0, 2.5, 3.0, 4.0, 5.0, 6.0, 7.0 and 8.0 hours each time replaced with an equal volume of fresh water. The samples were analyzed spectrophotometrically at 273 nm and from this analysis the amount of nonoxynol 9 was calculated. The results are shown in the attached drawing, which is a plot of the cumulative amount of nonoxynol 9 released, expressed as a percentage of the total originally present in the pores, as a function of time, demonstrating the controlled release character of the microbeads.

The foregoing description is directed primarily to preferred embodiments and practices of the present invention. It will be readily apparent to those skilled in the art that further changes and modifications in the actual implementation of the concepts described herein can be made without departing from the spirit and scope of the invention as defined by the following claims.

What is claimed is:

1. A composition of matter comprising a material provided with interstices having a solid particles residing therein, said material being a member selected from the group consisting of joined fibers, woven fabric, non-woven fabric, paper, woven cloth, non-woven cloth, foamed plastic and sponge, said solid particles being from about one to about 100 microns in diameter and containing a substantially continuous network of pores open to the exterior of said particles, with a functional substance retained in said pores.

2. A composition of matter in accordance with claim 1 in which said solid particles are substantially noncompressible.

3. A composition of matter in accordance with claim 1 in which said functional substance is an outwardly diffusible substance.

4. A composition of matter in accordance with claim 1 in which said functional substance is a low-melting solid.

5. A composition of matter in accordance with claim 1 in which said functional substance is a liquid.

6. A composition of matter in accordance with claim 1 in which said functional substance is a volatile liquid.

7. A composition of matter in accordance with claim 1 in which said functional substance is a substantially nonvolatile liquid.

8. A composition of matter in accordance with claim 1 in which said functional substance is a biologically active substance.

9. A composition of matter in accordance with claim 1 in which said functional substance is a biologically active substance selected from the group consisting of antiseptics, antibiotics, antifungals, anti-infectives, anesthetics pesticides spermicides, corticosteroids, vitamins, mildew retardants and antiacne agents.

10. A composition of matter in accordance with claim 1 in which said functional substance is a member selected from the group consisting of emollients, lubricants, moisturizers and sunscreens.

11. A composition of matter in accordance with claim 1 in which said functional substance is a member selected from the group consisting of deodorants and fragrance-bearing liquids.

12. A composition of matter in accordance with claim 1 in which said functional substance is a member selected from the group consisting of cleaning agents, disinfectants, polishes and waxes.

13. A composition of matter in accordance with claim 1 in which said solid particles have a total pore volume of about 0.1 cc/g to about 2.0 cc/g.

14. A composition of matter in accordance with claim 1 in which said solid particles have a surface area of about 1 m$^2$/g to about 400 m$^2$/g.

15. A composition of matter in accordance with claim 1 in which said solid particles have a pore diameter of about 0.003 micron to about 3.0 micron.

16. A composition of matter in accordance with claim 1 in which said solid particles are formed of a cross-linked polymer.

17. A composition of matter in accordance with claim 1 in which said solid particles are formed of a cross-linked copolymer of styrene and divinylbenzene.

18. A composition of matter in accordance with claim 1 in which said solid particles are formed of a cross-linked polymer of methyl methacrylate and ethylene glycol dimethacrylate.

19. A composition of matter in accordance with claim 1 in which said solid particles are compressible resilient particles and are the reaction product of cross-linking an ethylene-propylene-diene prepolymer.

20. A composition of matter in accordance with claim 1 in which said solid particles are compressible resilient particles and are the reaction product of cross-linking an ethylene-propylene-dicyclopentadiene prepolymer.

21. A composition of matter in accordance with claim 1 in which said solid particles are compressible.

22. A method for impregnating an intersticed material with a functional substance, said material being a member selected from the group consisting of joined fibers, woven fabric, non-woven fabric, paper, woven cloth, non-woven cloth, foamed plastic and sponge, said method comprising placing soldi particles in the interstices of said material, said solid particles being from about one to about 100 microns in diameter and containing a substantially continuous network of pores open to the exterior of said particles, said pores containing said functional substance.

23. A method in accordance with claim 22 in which said solid particles are compressible.

24. A method in accordance with claim 22 in which said solid particles are substantially noncompressible.

25. A method in accordance with claim 22 in which said solid particles have a total pore volume of about 0.1 cc/g to about 2.0 cc/g.

26. A method in accordance with claim 22 in which said solid particles have a surface area of about 1 m$^2$/g to about 400 m$^2$/g.

27. A method in accordance with claim 22 in which said solid particles have a pore diameter of about 0.003 micron to about 3.0 micron.

28. A method in accordance with claim 22 in which said solid particles are formed of a cross-linked polymer.

29. A method in accordance with claim 22 in which said solid particles are formed of a cross-linked copolymer of styrene and divinylbenzene.

30. A method in accordance with claim 22 in which said solid particles are formed of a cross-linked polymer of methyl methacrylate and ethylene glycol dimethacrylate.

31. A method in accordance with claim 22 in which said solid particles are compressible resilient particles and are the reaction product of cross-linking an ethylene-propylene-diene prepolymer.

32. A method in accordance with claim 22 in which said solid particles are compressible resilient particles and are the reaction product of cross-linking an ethylene-propylene-dicyclopentadiene prepolymer.

* * * * *